(12) United States Patent
Hanefeld et al.

(10) Patent No.: US 8,211,948 B2
(45) Date of Patent: Jul. 3, 2012

(54) LYOPHILIZED NANOEMULSION

(75) Inventors: Andrea Hanefeld, Heidelberg (DE); Martina Schmidt, Frankfurt am Main (DE); Simon Geissler, Arnstein (DE); Peter Langguth, Mainz (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 12/922,787

(22) PCT Filed: Feb. 26, 2009

(86) PCT No.: PCT/EP2009/001355
§ 371 (c)(1),
(2), (4) Date: Sep. 15, 2010

(87) PCT Pub. No.: WO2009/115175
PCT Pub. Date: Sep. 24, 2009

(65) Prior Publication Data
US 2011/0015266 A1   Jan. 20, 2011

(30) Foreign Application Priority Data
Mar. 20, 2008   (DE) .......................... 10 2008 015 366

(51) Int. Cl.
*A61K 9/107* (2006.01)
*A61K 9/19* (2006.01)
*A61K 47/14* (2006.01)
*A61K 47/26* (2006.01)

(52) U.S. Cl. ........ 514/943; 514/937; 514/938; 977/906; 977/907

(58) Field of Classification Search ............... 514/937, 514/938, 943; 977/906, 907
See application file for complete search history.

(56) References Cited

U.S. PATENT DOCUMENTS

| | | | |
|---|---|---|---|
| 4,616,047 A * | 10/1986 | Lafon | 523/105 |
| 6,638,519 B1 * | 10/2003 | Lorant | 424/401 |
| 2002/0193831 A1 | 12/2002 | Smith | |
| 2003/0147959 A1 | 8/2003 | Lambert et al. | |
| 2007/0213234 A1 * | 9/2007 | Yaghmur et al. | 508/110 |
| 2007/0269390 A1 * | 11/2007 | Inoue | 424/59 |

FOREIGN PATENT DOCUMENTS

| | | | |
|---|---|---|---|
| CN | 101428002 | * | 5/2009 |
| EP | 0159237 A1 | | 10/1985 |
| WO | WO 2005/110370 | * | 11/2005 |

OTHER PUBLICATIONS

World Intellectual Property Organization. "International Search Report" WO2009/115175 A3. Applicant: Merck GMBH. Mailed Nov. 25, 2009.

Toorisaka, Eiichi et al. "An enteric-coated dry emulsion formulation for oral insulin delivery." (Journal of Controlled Release), Sep. 20, 2005; pp. 91-96, vol. 107.

* cited by examiner

*Primary Examiner* — Brian P Mruk
(74) *Attorney, Agent, or Firm* — Millen, White, Zelano, Branigan, P.C.

(57) ABSTRACT

The present invention relates to a lyophilized nanoemulsion comprising a lipophilic phase and one or more sucrose fatty acid esters, to the nanoemulsion which can be prepared from the lyophilized nanoemulsion by redispersion, and to a process for the preparation of the lyophilized nanoemulsion.

18 Claims, 1 Drawing Sheet

LYOPHILIZED NANOEMULSION

The present invention relates to a lyophilised nanoemulsion comprising a lipophilic phase and one or more sucrose fatty acid esters, to the nanoemulsion which can be prepared from the lyophilised nanoemulsion by redispersion, and to a process for the preparation of the lyophilised nanoemulsion.

Emulsions are disperse systems which consist of two mutually immiscible liquids, of which one, the internal, dispersed phase, is finely distributed in the other, the external, continuous phase.

Nanoemulsions are emulsion systems in which the internal, dispersed, phase consists of very fine lipophilic droplets having a size in the range from about 20 to about 500 nm, which are homogeneously dispersed in the external phase consisting of water (O/W emulsion). Nanoemulsions can preferably be used parenterally and are used, in particular, for the intravenous nutrition of patients who are unable to take nutrition orally, commercially available brand products are, for example, Intralipid®, Lipodfundin®, Lipovenös®. All nanoemulsions have a milky/cloudy appearance.

Nanoemulsions should be differentiated from microemulsions, in which the internal, dispersed phase has a particle size of 10 nm to 50 nm. Microemulsions contain a significantly increased emulsifier concentration compared with nanoemulsions and usually also a co-emulsifier. Microemulsions are self-emulsifying and have a clear or opalescent appearance, but are not well tolerated as a consequence of the high emulsifier concentration and can therefore only be administered parenterally to a very limited extent.

Nanoemulsions which can be administered intravenously make high demands of the compatibility of their ingredients and the particle size of the fat particles. The fat component used in parenteral nutrition is preferably oils having a high content of unsaturated fatty acids, such as soybean, safflower and cotton oil, the emulsifiers used are lecithins, such as egg, soya and cerebral lecithin, and furthermore usually comprise antioxidants, such as tocopherol acetate, and optionally further assistants.

The emulsion is usually prepared by pre-emulsification of the warmed oil and water phases using a mixer, followed by microemulsification using a high-pressure homogeniser and subsequent sterilisation using superheated steam.

Nanoemulsions can be prepared quickly using standard comminution techniques (high-pressure homogenisation). However, nanoemulsions are thermodynamically unstable and therefore often have an inadequate shelf life. On storage over extended periods, in particular at elevated temperatures and in the case of temperature variations, coalescence of the fat particles occurs, with the consequence that the nanoemulsion overall becomes unusable.

The "Handbook on Injectable Drugs" (American Society of Hospital Pharmacists, page 237-244 (1986), Lawrence A. Trissel) describes some commercially available preparations. They comprise soybean oil or safflower oil, egg lecithin, glycerin and water and have average particle sizes of $\leq 0.5$ µm.

Nanoemulsions have also repeatedly been employed as carrier systems for lipophilic medicaments to be administered parenterally. The aim here is to increase the therapeutic efficacy and safety of medicaments by controlled release from emulsion systems (drug delivery system).

In accordance with their solubility properties, lipophilic active compounds present in nanoemulsions are partially or completely embedded in the fat particles. The pharmacokinetic behaviour of the active compound is thus crucially determined by the pharmacokinetic behaviour of the carrier preparations from which the active compound is first released. Delayed release avoids high local active-compound concentrations, reduces degradation and thus increases the duration of action. An example of a commercially available nanoemulsion comprising an active compound is Diazepam®-Lipuro.

All commercially available nanoemulsions comprise lecithin as emulsifier. Since lecithin is sensitive to hydrolysis, and the hydrolysis product lysolecithin can cause hemolysis, the pH of the emulsions must be adjusted by means of NaOH or Na oleate, and/or assistants which inhibit hydrolysis must be added. In general, assistants which are not justified from the point of view of the application and merely serve for stabilisation should be avoided whenever possible in order basically to exclude the potential risk of damage arising due to them.

JP 11171796 A describes the preparation of an emulsion for oral administration which comprises the active compound teprenone and comprises a sucrose fatty acid ester as emulsifier. The aim of the development described is to protect the oxidation-sensitive active compound against degradation and to provide a palatable preparation for oral administration. Freeze-drying of the emulsion is not described.

U.S. Pat. No. 5,705,142 describes a lyophilised nanoemulsion which is said to be suitable also for parenteral administration. Besides the fat phase and the emulsifier, the lyophilised emulsion comprises at least 40% by weight of an (amine) cryoprotection agent. Besides lecithin as emulsifier, all emulsions of the working examples comprise a co-emulsifier and α-tocopherol as antioxidant. Furthermore, polyvinylpyrrolidone (PVP) is usually present, which is intended, as suspension medium, to control the droplet size of the reconstituted emulsion and to keep it in the nanoscale range.

WO 94/14418 A1 describes a lyophilised emulsion composition whose internal, lipophilic phase consists of hydrophilic emulsifiers and acetylated monoglycerides, and which furthermore comprises sugars or sugar alcohols as cryoprotection agent/structure former. Acetylated monoglycerides have an amphiphilic action and are therefore unacceptable from a toxicological point of view. Furthermore, the emulsion composition comprises high proportions of sugars/sugar alcohols (the sugar:emulsifier+acetylated monoglycerides weight ratio in the working examples is 2:1), meaning that reconstitution enables the preparation either of hyperosmotic and thus poorly tolerated emulsions or alternatively of emulsions having only a low proportion of lipophilic phase.

JP 52-96724 describes lyophilised O/W emulsions which, besides an oil/fat and emulsifiers, comprise a film-forming assistant, such as, for example, gelatine, PVP, methylcellulose, PVA, polyethylene glycol or sucrose fatty acid ester. Both the starting emulsions initially prepared (before freeze-drying) and the emulsions redispersed from the lyophilised emulsion have droplet sizes in the two-digit µm range. Furthermore, a significant increase in the particle size compared with the starting emulsion arises after freeze-drying and redispersion. The emulsions are not suitable for parenteral administration.

JP 2004/161650 A describes a freeze-dried W/O/W emulsion comprising polyglycerol fatty acid ester or sucrose fatty acid ester as emulsifier, whose external phase comprises polyvinyl alcohol or xanthan gum and a sugar. Without polyvinyl alcohol or xanthan gum, the lyophilised W/O/W emulsions cannot be redispersed to give emulsions, W/O/W emulsions having average particle sizes of about 500 to >3000 nm arise after redispersion of the emulsions comprising these substances. The redispersed W/O/W emulsions are suitable for oral administration, but not for parenteral administration.

A paper recently published on the internet (Dong Zhao et al.: A submicron emulsion for intravenous injection: Characterization, in vitro and in vivo anti-tumor effect, Int J Pharm (2007), doi:10.1016/j.ijpharm.2008.01.055) discloses a freeze-dried nanoemulsion which, besides an oil and lecithin as emulsifier, comprises a high proportion of sucrose (oil phase:sugar weight ratio=1:5). Owing to the use of hydrolysis-sensitive lecithin, the emulsion additionally comprises vitamin E. The high proportion of sucrose may disadvantageously result in hypertonic solutions after redispersion. Furthermore, the sugar content is not uncritical on administration to diabetics and may result in hyperosmotic formulations.

The object of the present invention was to remedy the disadvantages of the prior art and to provide a nanoemulsion which can be lyophilised and can be redispersed by redispersion with water to give a nanoemulsion which can be administered parenterally and has a droplet size distribution corresponding to the starting emulsion. The lyophilised nanoemulsion should have the simplest possible structure and should also be capable of being prepared without the addition of further substances, such as cryoprotection agents and antioxidants, and should be capable of storage in a stable manner over long periods (shelf life 3 years).

Surprisingly, it has been found that a lyophilised nanoemulsion which meets these requirements can be provided if it comprises sucrose fatty acid esters as emulsifiers besides a lipid. The invention therefore relates to a lyophilised nanoemulsion which is characterised in that it comprises at least one lipid and at least one sucrose fatty acid ester.

Owing to the stability of the sucrose fatty acid esters, it is advantageous that neither a pH adjustment (alkalization) nor the addition of an antioxidant is necessary. Surprisingly, the lyophilised nanoemulsion can be prepared even without addition of cryoprotection agents and can nevertheless be redispersed by addition of an aqueous liquid to give a nanoemulsion whose particle size distribution substantially corresponds to that of the starting emulsion. As a consequence of the possible omission of cryoprotection agent, the risk of microbial contamination is reduced (the additives promote microbial growth). Accordingly, according to a preferred embodiment, the nanoemulsion according to the invention comprises no cryoprotection agents, such as, for example, sugars, sugar alcohols or amino acids.

It is furthermore advantageous that the lyophilised nanoemulsion can also be redispersed (by addition of a little water) to give a nanoemulsion which has an increased proportion of internal (lipid) phase compared with the starting emulsion, without this being accompanied by increased osmolality, which calls into question the overall potential for parenteral administration (hyperosmotic nanoemulsions are poorly tolerated parenterally).

The incorporation of lipophilic active compounds enables the lyophilised nanoemulsion according to the invention advantageously also to be employed as drug delivery system which can be administered parenterally or also orally after redispersion with an aqueous liquid. In addition, the lyophilised nanoemulsion is also suitable, for example, as carrier emulsion for parenteral fat substitution therapy.

According to an embodiment of the invention, the lyophilised nanoemulsion comprises one or more active compounds. The invention therefore also relates to a lyophilised nanoemulsion which is characterised in that it comprises at least one lipid, at least one sucrose fatty acid ester and at least one active compound.

Preference is given to lipophilic active compounds, i.e. substances which are relatively insoluble in water, but are soluble in one or more fatty solvents, such as, for example, benzene, chloroform, acetone, ether or hexane. Preference is given to pharmaceutically active substances which have a solubility of preferably >1 µg/ml in fats/oils (triesters of the trihydric alcohol glycerol with saturated/unsaturated monocarboxylic acids of various chain length) and an oil/water distribution ratio of >1:1. Examples of lipophilic active compounds which may be present in the lyophilised nanoemulsion according to the invention, (fibrates, for example fenofibrate/clofibrate, benzodiazepines, for example carbamazepine, azoles, for example bifonazole, steroids, for example danazole).

The lyophilised nanoemulsion can be redispersed with an aqueous liquid, preferably water, to give a nanoemulsion whose particle size distribution substantially corresponds to the particle size distribution of the starting emulsion (i.e. the nanoemulsion before conversion into the lyophilised nanoemulsion by means of freeze-drying). Besides pure water, in particular water for injection, the aqueous liquid used for the redispersion may also comprise dissolved substances, for example isotonic agents, such as saline or dextrose. Aqueous liquids which are particularly suitable for redispersion are physiological saline solution and dextrose solutions.

The lyophilised emulsion according to the invention can basically comprise, as lipid, all lipids which are suitable from a pharmaceutical point of view for the preparation of nanoemulsions, in particular mono-, di- and/or triglycerides with $C_8$- to $C_{22}$-fatty acids, particularly preferably $C_8$- to $C_{18}$-fatty acids, and/or fat-soluble vitamins. The invention therefore also relates to a lyophilised nanoemulsion which is characterised in that mono-, di- and/or triglycerides with $C_8$- to $C_{22}$-fatty acids, preferably $C_8$- to $C_{18}$-fatty acids, unsaturated or saturated $C_8$- to $C_{22}$-fatty acids and/or fat-soluble vitamins or fat-soluble active compounds, preferably, are present as lipid.

Examples of suitable lipids are natural oils, such as, for example, groundnut oil, almond oil, olive oil, sesame oil, soybean oil, thistle oil (safflower oil) or cotton oil, semisynthetic oils, such as, for example, medium-chain triglycerides (MCTs), a triglyceride mixture which comprises principally $C_8$- to $C_{12}$-fatty acids, in particular caprylic acid and capric acid, as fatty acids, but also the fat-soluble vitamins (vitamin A, vitamin D, vitamin E, vitamin K) of which vitamin E and vitamin D are preferred.

The lyophilised nanoemulsion preferably comprises triglycerides as lipid. Particularly preferred triglycerides are triglycerides of $C_8$- to $C_{12}$-fatty acids.

Sucrose fatty acid esters are esters which can be obtained, for example, by transesterification of sucrose using methyl esters of long-chain fatty acids. Sucrose esters which can be employed in accordance with the invention are those with $C_8$- to $C_{22}$-fatty acids, preference is given to sucrose esters with $C_{12}$- to $C_{18}$-fatty acids, in particular lauric, myristic, palmitic and stearic acid, particular preference is given to lauric and myristic acid. Sucrose fatty acid esters are also commercially available and are marketed, for example, by Mitsubishi Kagaku Corp., Tokyo, Japan, under the trade name Ryoto. Examples thereof are sucrose fatty acid esters with lauric acid, with myristic acid or with stearic acid, which have the trade names Ryoto L 1695, Ryoto M 1695 and Ryoto S 1670.

According to an advantageous embodiment of the lyophilised nanoemulsion, the lipid present therein and the sucrose fatty acid esters are present in a weight ratio of 1:1 to 5:1, preferably in a weight ratio of 2:1 to 4:1, to one another. The invention therefore also relates to a lyophilised nanoemulsion which is characterised in that lipid and sucrose fatty acid ester are present in a weight ratio of 1:1 to 5:1, preferably in a weight ratio of 2:1 to 4:1, to one another.

The lyophilised nanoemulsion according to the invention can be prepared by freeze-drying a nanoemulsion in which lipid is dispersed in an aqueous phase together with the emulsifier. Lipid and aqueous phase are advantageously present in a weight ratio of 0.5:99.5 to 30:70 to one another in the nanoemulsion to be lyophilised (starting emulsion). The invention therefore also relates to a lyophilised nanoemulsion which is characterised in that it is prepared by freeze-drying a nanoemulsion in which lipid and aqueous phase are present in a weight ratio of 0.5:99.5 to 30:70 to one another.

The lyophilised nanoemulsion can be redispersed in a simple manner by addition of an aqueous liquid to a nanoemulsion which can be administered directly, for example parenterally or orally. The invention therefore also relates to a nanoemulsion which is characterised in that it is prepared from the lyophilised nanoemulsion by redispersion with an aqueous liquid.

Depending on the amount of aqueous liquid added for redispersion of the lyophilised emulsion, the ratio of lipid and aqueous liquid to one another in the nanoemulsion formed by redispersion can be varied over broad ranges. If, for example, a little aqueous liquid is used, highly concentrated nanoemulsions are formed which comprise large amounts of active compound per unit volume on charging with active compound. This also enables the administration of large amounts of active compound by means of small volumes. Thus, if high active-compound doses are to be administered, the injection volume necessary for this purpose can advantageously be significantly reduced and, for example, intravenous infusion can be replaced by intravenous injection. Since the lyophilised nanoemulsion also requires no cryoprotection agent, such as, for example, sugar, redispersion thereof can also be carried out with little aqueous liquid without this inevitably becoming hypertonic, like the lyophilised emulsions of the prior art, which results, for example on parenteral administration, in the known toleration problems.

The invention therefore also relates to a nanoemulsion which is characterised in that lipid and water are present therein in a weight ratio of 0.5:99.5 to 50:50, preferably in a weight ratio of 5:95 to 50:50, to one another.

The lyophilised nanoemulsion according to the invention can be prepared by removing the aqueous phase from an emulsion prepared by means of the processes and technologies which are customary in medicament production by lyophilisation. The invention therefore also relates to a process for the preparation of the lyophilised nanoemulsion according to the invention, which is characterised in that firstly a nanoemulsion is prepared in a conventional manner, and the external, aqueous phase is subsequently removed therefrom by means of freeze-drying.

If it is intended to incorporate active compounds into the lyophilised nanoemulsion according to the invention, this can be carried out in the case of hydrophilic active compounds by dissolution in the aqueous surfactant phase (emulsifier boundary layer and emulsifier micelles) and in the case of lipophilic active compounds by dissolution in the phase comprising emulsifier and lipid. Alternatively, the active compound can also be added immediately before the lyophilisation is carried out, which is particularly advantageous for hydrolysis-sensitive and/or thermolabile active compounds. The process for the preparation of the active compound-containing emulsion composition according to the invention can thus advantageously be adapted to the physicochemical properties of the active compounds. In an advantageous embodiment of the process according to the invention, at least one active compound is therefore dissolved, before emulsification, either in the aqueous phase or in the emulsifier- and lipid-containing phase or at least one active compound is added to the emulsion before freeze-drying thereof.

It should be noted here that the active-compound distribution within the disperse system before lyophilisation is guaranteed, which can easily be checked using conventional methods, such as equilibrium dialysis, differential dialysis and ultrafiltration.

Figure 1:
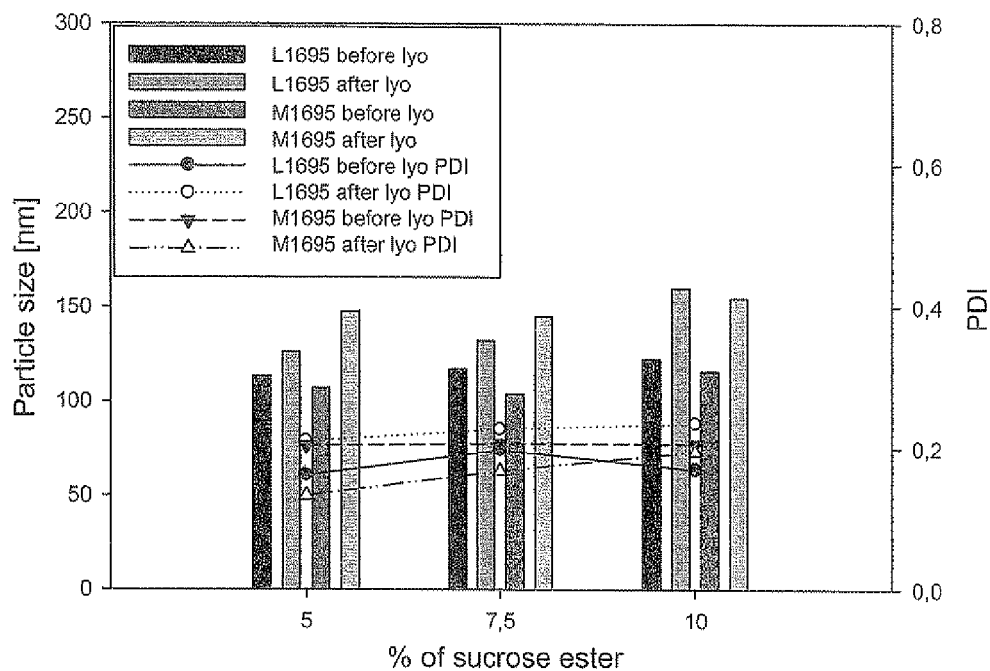
FIGS. 1 and 2 are graphs.

The examples explain the invention without being restricted thereto.

EXAMPLES

General Process for the Preparation of Nanoemulsions

The sucrose ester is dissolved in $H_2O$ at 50° C., the oil is held at a temperature of 50° C., water and oil phase are combined with one another, the combined phases are pre-homogenised for 3 minutes by means of an Ultraturrax at 8000 rpm and subsequently subjected to high-pressure homogenisation in an Avestin Emulsiflex-C3 (8 cycles, 4×1000 bar+4×2000 bar).

The nanoemulsion is subsequently subjected to the following freeze-drying process:
1) Freezing process: −50° C., 3.5 hours
2) Main drying: −40° C., suitable reduced pressure over up to 48 hours
3) Post-drying: −40-+20° C., suitable reduced pressure over up to 12 hours.

Example 1

Using the substances indicated below, a nanoemulsion is prepared in accordance with the general process described above.

| | |
|---|---|
| Sucrose lauric acid ester (Ryoto L1695) | 5 g |
| Medium-chain triglycerides | 10 g |
| Water | 85 g |

Example 2

Using the substances indicated below, a nanoemulsion is prepared in accordance with the general process described above.

| | |
|---|---|
| Sucrose lauric acid ester (Ryoto L1695) | 5 g |
| Soya oil | 10 g |
| Water | 85 g |

Example 3

Using the substances indicated below, a nanoemulsion is prepared in accordance with the general process described above.

| Sucrose myristic acid ester (Ryoto M1695) | 5 g |
| Medium-chain triglycerides | 10 g |
| Water | 85 g |

Example 4

Using the substances indicated below, a nanoemulsion is prepared in accordance with the general process described above.

| Sucrose lauric acid ester (Ryoto L1695) | 5 g |
| Medium-chain triglycerides | 20 g |
| Water | 75 g |

Example 5

Using the substances indicated below, a nanoemulsion are prepared in accordance with the general process described above.

| Sucrose stearic acid ester (Ryoto S1670) | 5 g |
| Medium-chain triglycerides | 20 g |
| Water | 75 g |

Example 6

Using the substances indicated below, a nanoemulsion is prepared in accordance with the general process described above.

| Sucrose lauric acid ester (Ryoto L1695) | 5 g |
| Medium-chain triglycerides | 30 g |
| Water | 65 g |

Example 7

Using the substances indicated below, a nanoemulsion is prepared in accordance with the general process described above.

| Sucrose lauric acid ester (Ryoto L1695) | 7.5 g |
| Medium-chain triglycerides | 30 g |
| Water | 62.5 g |

Example 8

Using the substances indicated below, a nanoemulsion is prepared in accordance with the general process described above.

| Sucrose lauric acid ester (Ryoto L1695) | 10 g |
| Medium-chain triglycerides | 30 g |
| Water | 60 g |

Example 9

Using the substances indicated below, a nanoemulsion is prepared in accordance with the general process described above.

| Sucrose lauric acid ester (Ryoto L1695) | 7.5 g |
| Medium-chain triglycerides | 10 g |
| Water | 82.5 g |

Example 10

Using the substances indicated below, a nanoemulsion is prepared in accordance with the general process described above.

| Sucrose lauric acid ester (Ryoto L1695) | 10 g |
| Medium-chain triglycerides | 10 g |
| Water | 80 g |

Example 11

Using the substances indicated below, a nanoemulsion is prepared in accordance with the general process described above.

| Sucrose lauric acid ester (Ryoto M1695) | 7.5 g |
| Medium-chain triglycerides | 10 g |
| Water | 82.5 g |

Example 12

Using the substances indicated below, a nanoemulsion is prepared in accordance with the general process described above.

| Sucrose lauric acid ester (Ryoto M1695) | 10 g |
| Medium-chain triglycerides | 10 g |
| Water | 80 g |

Example 13

Nanoemulsion Comprising Active Compound

Using the substances indicated below, a nanoemulsion is prepared in accordance with the general process described above.

| Sucrose lauric acid ester (Ryoto L1695) | 7.5 g |
| Medium-chain triglycerides | 30 g |
| Fenofibrate | 1.5 g |
| Water | 61 g |

Comparative Example 1

Using the substances indicated below, a nanoemulsion is prepared in accordance with the general process described above.

| | |
|---|---|
| PEG660-12-hydroxystearate (Solutol HS15) | 5 g |
| Medium-chain triglycerides | 10 g |
| Water | 85 g |

Comparative Example 2

Using the substances indicated below, a nanoemulsion is prepared in accordance with the general process described above.

| | |
|---|---|
| Phosphatidylcholine, soya-based, 75% purity): | 5 g |
| Soya oil | 10 g |
| Water | 85 g |

Nanoemulsions are prepared analogously to the general process described above using Solutol® HS 15 (PEG660-12-hydroxystearate)/Cremophor® RH 40 (PEG-40 hydrogenated castor oil)/Lipoid S75 (soya-based phosphatidylcholine) and Lipoid E80 (egg-based phosphatidyl choline) as emulsifiers and medium-chain triglycerides (MCTs) as lipid (proportions by weight see Table 2) and freeze-dried. In addition, a commercially available nanoemulsion (Lipovenös®, comprising phosphatidyl choline as emulsifier) is lyophilised under the same conditions.

None of the lyophilisates obtained (lyophilised nanoemulsions) has an intact lyophilisation cake, all are collapsed. On redispersion with water, phase separation occurs or very coarse emulsions are formed which are not suitable for parenteral administration.

By contrast, the nanoemulsions comprising sucrose fatty acid esters exhibit structure-retaining cake formation after lyophilisation. On addition of water to the lyophilisation cake, nanoemulsions which have particle sizes in the range <200 nm form without input of energy.

The size measurements are carried out by means of photon correlation spectroscopy. The intensity-weighted average diameter of the emulsion droplets is determined in a Zeatasizer Nano ZS (Malvern Ltd, UK). The scatter signals are evaluated via the DTS 5.03 software (Malvern Ltd. UK). The polydispersity index (PDI) is implemented in this software as a measure of the size distribution of the sample.

The average particle sizes and the polydispersity index (PDI) of the emulsions comprising sucrose fatty acid esters before and after freeze-drying are shown in Table 1 and depicted graphically in FIG. 1.

TABLE 1

| Example No. | Emulsifier Ryoto L1695 [%] | Lipid MCT [%] | Before freeze-drying Particle size [nm] | PDI | After freeze-drying Particle size [nm] | PDI |
|---|---|---|---|---|---|---|
| 1 | 5 | 10 | 113.4 | 0.162 | 126.2 | 0.21 |
| 9 | 7.5 | 10 | 117.1 | 0.198 | 132.1 | 0.227 |
| 10 | 10 | 10 | 122.2 | 0.17 | 159.7 | 0.235 |

| | Emulsifier Ryoto M1695 [%] | Lipid MCT [%] | Before freeze-drying Particle size [nm] | PDI | After freeze-drying Particle size [nm] | PDI |
|---|---|---|---|---|---|---|
| 3 | 5 | 10 | 106.9 | 0.204 | 147.5 | 0.133 |
| 11 | 7.5 | 10 | 103.8 | 0.207 | 144.9 | 0.168 |
| 12 | 10 | 10 | 116 | 0.206 | 154.6 | 0.195 |

Figure 2:
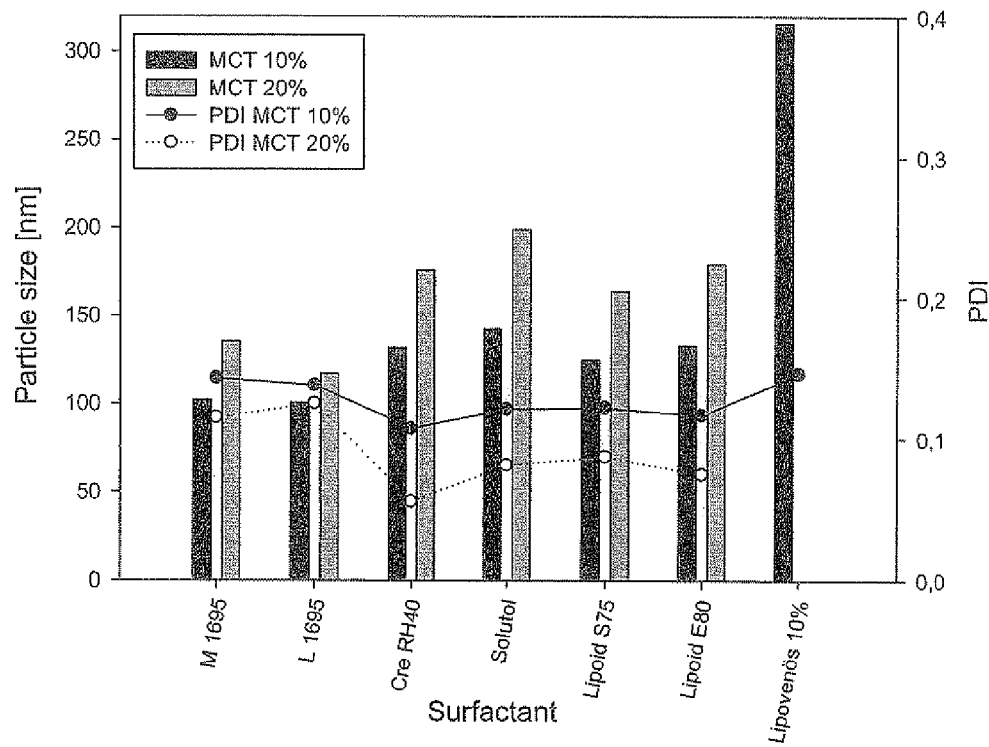

FIG. 2 and Table 2 show the particle sizes of representative nanoemulsions before lyophilisation on the basis of the present invention compared with standard emulsions. Surprisingly, sucrose fatty acid esters result in up to ~50 nm smaller emulsion droplets than the emulsifiers usually used for nanoemulsions for the same energy input and the same surfactant concentration.

TABLE 2

| | MCT 10% | | MCT 20% | |
|---|---|---|---|---|
| Surfactant/product | Size [nm] | PDI | Size [nm] | PDI |
| Ryoto M 1695 2% | 101.9 | 0.143 | 135.3 | 0.115 |
| Ryoto L 1695 2% | 100.6 | 0.138 | 117 | 0.125 |
| Cremophor RH 40 2% | 131.7 | 0.107 | 175.8 | 0.056 |
| Solutol HS 15 2% | 142.7 | 0.121 | 199 | 0.081 |
| Lipoid S75 | 125 | 0.122 | 163.9 | 0.087 |
| Lipoid E80 | 133.1 | 0.117 | 179.6 | 0.075 |
| Lipovenös ® 10% | 316.2 | 0.146 | — | |

The invention claimed is:

1. A lyophilised nanoemulsion, comprising at least one lipid and at least one sucrose fatty acid ester, wherein said lipid and sucrose fatty acid ester are present in a weight ratio of 1:1 to 5:1 to one another.

2. A lyophilised nanoemulsion according to claim 1, further comprising at least one active compound.

3. A lyophilised nanoemulsion according to claim 1, wherein said lipid is a mono-, di- and/or triglyceride with a $C_8$- to $C_{22}$-fatty acid and/or a fat-soluble vitamin.

4. A lyophilised nanoemulsion according to claim 3, wherein said lipid is a triglyceride.

5. A lyophilised nanoemulsion according to claim 4, wherein said triglyceride is a $C_8$- to $C_{12}$-fatty acid.

6. A lyophilised nanoemulsion according to claim 1, wherein said sucrose fatty acid comprises a $C_8$- to $C_{22}$-fatty acid.

7. A lyophilised nanoemulsion according to claim 1, wherein said lyophilised nanoemulsion is prepared by freeze-drying a nanoemulsion in which lipid and aqueous-phases are present in a weight ratio of 0.5:99.5 to 30:70.

8. A lyophilised nanoemulsion wherein said lyophilised nanoemulsion according to claim 1, is prepared by redispersion with water.

9. A lyophilised nanoemulsion according to claim 8, wherein said lipid and water are present therein in a weight ratio of 0.5:99.5 to 50:50, to one another.

10. A process for the preparation of the lyophilised nanoemulsion according to claim 1, comprising preparing a nanoemulsion having an external aqueous phase and subsequently removing the external aqueous phase therefrom by means of freeze-drying.

11. A process according to claim 10, comprising dissolving at least one active compound before emulsification, either in the aqueous phase or in the lipid-containing phase
   or
   adding at least one active compound to the emulsion before freeze-drying thereof.

12. A nanoemulsion according to claim 3, wherein said lipid is Vitamin E or Vitamin D.

13. A nanoemulsion according to claim 1, wherein said lipid is groundnut oil, almond oil, olive oil, sesame oil, soybean oil, thistle oil, safflower oil, cotton oil, a medium-chain triglyceride (MCTs), a triglyceride.

14. A nanoemulsion according to claim 1, wherein said sucrose fatty acid ester is lauric, myristic, palmitic and/or stearic acid.

15. A nanoemulsion according to claim 1, wherein said nanoemulsion contains no antioxidants.

16. A nanoemulsion according to claim 1, wherein said nanoemulsion comprises no sugar cryoprotection agent, sugar alcohol cryoprotection agent or amino acid cryoprotection agent.

17. A nanoemulsion according to claim 1, wherein said lipid and sucrose fatty acid ester are present in a weight ratio of 2:1 to 4:1, to one another.

18. A lyophilised nanoemulsion according to claim 9, wherein said lipid and water are present therein in a weight ratio of 5:95 to 50:50, to one another.

* * * * *